United States Patent [19]

Sauer et al.

[11] 4,224,254

[45] Sep. 23, 1980

[54] PREPARATION OF AROMATIC AND ARALIPHATIC ALDEHYDES

[75] Inventors: Wolfgang Sauer, Mannheim; Werner Fliege, Otterstadt; Christian Dudeck, Limburgerhof; Norbert Petri, Frankenthal, all of Fed. Rep. of Germany

[73] Assignee: BASF Aktiengesellschaft, Fed. Rep. of Germany

[21] Appl. No.: 24,830

[22] Filed: Mar. 28, 1979

[30] Foreign Application Priority Data

Apr. 21, 1978 [DE] Fed. Rep. of Germany ....... 2817496

[51] Int. Cl.$^2$ ............................................. C07C 45/16
[52] U.S. Cl. .................................... 568/431; 260/577
[58] Field of Search .............. 260/603 C, 599, 600 R, 260/577

[56] References Cited

U.S. PATENT DOCUMENTS

| | | | |
|---|---|---|---|
| 1,968,552 | 7/1934 | Bond et al. | 260/603 C |
| 2,918,497 | 12/1959 | Walter | 260/600 R |

FOREIGN PATENT DOCUMENTS

1294360  5/1969  Fed. Rep. of Germany ....... 260/603 C

OTHER PUBLICATIONS

Houben-Weyl, Methoden der Organischen Chemie, vol. 7/1.
Ullmanns Encyklopadie der technischen Chemie, 4th ed., vol. 8, pp. 344–350 and 436.

*Primary Examiner*—Bernard Helfin
*Attorney, Agent, or Firm*—Keil & Witherspoon

[57] ABSTRACT

Aromatic and araliphatic aldehydes are prepared by oxidizing corresponding alcohols with oxygen in the presence of a silver catalyst of a defined particle size, and under defined temperature conditions. The products are starting materials for the preparation of dyes, pesticides, plastics and scents.

12 Claims, No Drawings

PREPARATION OF AROMATIC AND ARALIPHATIC ALDEHYDES

The present invention relates to a process for the preparation of aromatic and araliphatic aldehydes by oxidizing corresponding alcohols with oxygen in the presence of a silver catalyst of a defined particle size, and under defined temperature conditions.

Houben-Weyl, Methoden der Organischen Chemie, volume 7/1, pages 159-191, discloses that alcohols can only be converted to the corresponding aldehydes with good results if specific oxidizing agents and/or catalysts and conditions are selected in accordance with the structure of the alcohol. For example, chromic acid is recommended as advantageous for the preparation of aliphatic aldehydes (loc. cit., page 171) and selenium dioxide (loc. cit., page 179) or nitric acid for the preparation of aromatic aldehydes, such as benzaldehyde. In the case of the catalytic dehydrogenation of alcohols, copper, silver and zinc compounds are mentioned particularly for use with methanol (loc. cit., page 160). Houben-Weyl states (loc. cit., page 164) that "with higher alcohols (even starting with $C_8$) there is a substantial decrease in the yield of aldehyde, probably due to deposition of tar on the catalyst". It is also pointed out that benzyl alcohols are more difficult to dehydrogenate than aliphatic alcohols; they tend to form ethers easily and the corresponding aromatic aldehydes eliminate carbon monoxide more easily. Hence, it is recommended that the dehydrogenation be carried out under reduced pressure over a pure copper or silver metal catalyst, and it is stated that "taking all precautionary measures, benzaldehydes are obtained, at 300° C., in yields of up to 80% of theory" (loc. cit., page 166). To prepare silver catalysts, spongy silver is used, or silver oxide is reduced with hydrogen at 400°-500° C. (loc. cit., page 162). Zinc oxide on pumice is recommended as the catalyst for the dehydrogenation of phenylethyl alcohol, but gives a yield of only 50 percent at 430° C.

Ullmanns Encyklopädie der technischen Chemie, 4th edition, volume 8, page 436, also mentions 200°-300° C. as the reaction temperatures for the dehydrogenation of benzyl alcohol over copper catalysts, and states that at 380° C. carbon monoxide, carbon dioxide, benzene and toluene are also formed. It is stated, in general terms, that only the oxidation of toluene and the side chain chlorination of toluene to benzal chloride, with subsequent hydrolysis, have achieved industrial importance for the preparation of benzaldehyde (Ullmann, loc. cit., pages 344-350).

We have found that aromatic and araliphatic aldehydes can be produced advantageously by continuous oxidation of araliphatic alcohols in the presence of a metal catalyst at an elevated temperature, if araliphatic alcohols are oxidized with oxygen in the presence of silver crystals of particle size from 0.1 to 2.5 millimeters at from 450° to 700° C.

Where benzyl alcohol is used, the reaction can be represented by the following equations:

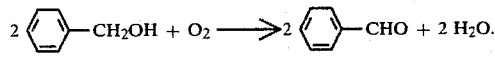

In comparison to the conventional processes, the process of the invention surprisingly gives, more simply and more economically, a better overall result in respect of yield and purity of the aromatic and araliphatic aldehydes and in respect of the life of the catalyst. The space-time yield is also better. Involved preparation or pretreatment of the catalyst is avoided. Unconverted alcohol can be isolated on distilling the reaction mixture, and be recycled to the synthesis. Compared to conventional processes, the novel process offers the possibility of preparing a plurality of differently substituted aromatic and araliphatic aldehydes, by a single method and in a single installation, without having to modify the apparatus. The oxidizing agent used, namely air, is cheap and easily handled and, in contrast to other oxidizing agents, presents no waste disposal problems.

Compared to the catalyst used in conventional processes, the catalyst of the invention has a substantially longer life and can be obtained more simply and more economically. Silver crystals of all particle sizes, including those obtained from the electrolytic preparation of silver granules, may be used. Accordingly, the process of the invention permits better utilization of the electrolysis installation in which the silver is produced, which can thus be made correspondingly smaller. There is a saving in energy, personnel requirements and auxiliaries, eg. nitric acid, and operations such as washing, sieving and drying the silver are simplified. In the conventional processes, the silver must additionally be applied to a carrier or must be metered before it can be added. All these advantageous results of the process according to the invention are surprising. It could not have been expected, in view of the prior art, that the use of pure silver crystals of a special particle size instead of the use of spongy silver, silver on carriers, or other catalysts, would permit an increase in the rate of reaction and hence in the space-time yield, and in particular at substantially higher temperatures. The advantageous results are furthermore particularly surprising in view of the information in Houben-Weyl, since the high temperatures used according to the invention would have led to the expectation of at least a substantial diminution in the yield and a substantial formation of decomposition products. The process of the invention avoids the expense of working under reduced pressure and using a special catalyst treatment. High specific throughput rates, for example from 0.1 to 3 tonnes/m² of catalyst cross-section per hour, can be achieved.

Aromatic and araliphatic aldehydes which can advantageously be prepared are those of the formula

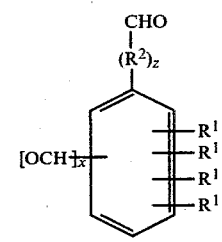

and, accordingly, advantageous araliphatic alcohol starting materials are those of the formula

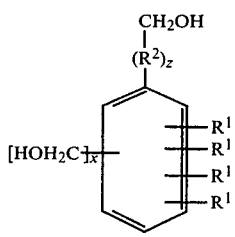

where the individual radicals $R^1$ may be identical or different and each is hydrogen, an aliphatic radical, $R^3$—O— or

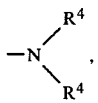

$R^2$ is an aliphatic radical, $R^3$ is hydrogen or an aliphatic radical, x and z may be identical or different and each is 0 or 1, and the individual radicals $R^4$ may be identical or different and each is an aliphatic radical. Preferred starting materials II and accordingly preferred end products I are those where the individual radicals $R^1$ are identical or different and each is hydrogen or alkyl of 1 to 5 carbon atoms, $R^3$—O— or

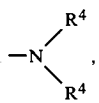

$R^2$ is alkylene of 1 to 5 carbon atoms, $R^3$ is hydrogen or alkyl of 1 to 5 carbon atoms, the individual radicals $R^4$ are identical or different and each is alkyl of 1 to 5 carbon atoms and x and z are identical or different and each is 0 or 1. Since the reaction is carried out in the gas phase, alcohols II which are easily vaporizable without decomposition are generally used. The above radicals may in addition be substituted by groups which are inert under the reaction conditions, for example alkyl of 1 to 4 carbon atoms. Aromatic aldehydes, for the purposes of the invention, means those aldehydes of the above formula where z is 0 and hence $(R^2)_z$ is a single bond, whilst araliphatic aldehydes are those where z is 1; in both cases, the starting materials II are araliphatic alcohols. Advantageously, monoalcohols (x=0) or dialcohols (x=1) are used as the starting materials II.

Examples of suitable starting materials II are 2-methylbenzyl alcohol, 3-methylbenzyl alcohol, 4-methylbenzyl alcohol, 2-methoxybenzyl alcohol, 3-methoxybenzyl alcohol, 4-methoxybenzyl alcohol, 2,3-dimethylbenzyl alcohol, 3,4-dimethylbenzyl alcohol, 2,6-dimethylbenzyl alcohol, 3,5-dimethylbenzyl alcohol, 2,3-dimethoxybenzyl alcohol, 3,4-dimethoxybenzyl alcohol, 3,5-dimethoxybenzyl alcohol, 2-ethylbenzyl alcohol, 3-ethylbenzyl alcohol, 4-ethylbenzyl alcohol, 2,3-diethylbenzyl alcohol, 3,4-diethylbenzyl alcohol, 2,6-diethylbenzyl alcohol, 3,5-diethylbenzyl alcohol, 2-ethoxybenzyl alcohol, 3-ethoxybenzyl alcohol, 4-ethoxybenzyl alcohol, 2-n-propylbenzyl alcohol, 3-n-propylbenzyl alcohol, 4-n-propylbenzyl alcohol, 2,3-di-n-propylbenzyl alcohol, 3,4-di-n-propylbenzyl alcohol, 2,6-di-n-propylbenzyl alcohol, 3,5-di-n-propylbenzyl alcohol, 2-isopropylbenzyl alcohol, 3-isopropylbenzyl alcohol, 4-isopropylbenzyl alcohol, 2-butylbenzyl alcohol, 3-butylbenzyl alcohol, 4-butylbenzyl alcohol, 2-isobutylbenzyl alcohol, 3-isobutylbenzyl alcohol, 4-isobutylbenzyl alcohol, 2-tert.-butylbenzyl alcohol, 3-tert.-butylbenzyl alcohol, 4-tert.-butylbenzyl alcohol, 2,3-diethoxybenzyl alcohol, 3,4-diethoxybenzyl alcohol, 2,6-diethoxybenzyl alcohol, 3,5-diethoxybenzyl alcohol and benzyl alcohol; 2,3,4-trimethoxybenzyl alcohol, 3,4,5-trimethoxybenzyl alcohol, 2,4,6-trimethoxybenzyl alcohol and corresponding trihydroxybenzyl alcohols etherified with an ethyl, n-propyl, isopropyl, n-butyl, sec.-butyl, isobutyl or tert.-butyl group; o-, m- and p-aminobenzyl alcohols in which the phenyl ring may be unsubstituted or substituted as above, and in which the nitrogens are disubstituted, the substituents being methyl, ethyl, n-propyl, isopropyl, n-butyl, sec.-butyl, isobutyl and tert.-butyl; o-, m- and p-hydroxymethyl-benzyl alcohol and corresponding di-(hydroxymethyl)-benzenes which are nuclear-substituted as above; and phenylethyl, phenylpropyl, phenylisopropyl, phenylbutyl, phenyl-sec.-butyl, phenyl-tert.-butyl, phenylisobutyl, phenylpentyl, phenylhexyl and phenylisopentyl alcohols, which are unsubstituted or substituted as above.

The starting materials II may also be used as a mixture with water; the aqueous mixtures can advantageously contain from 30 to 100 percent by weight, preferably from 70 to 90 percent by weight, of starting material II. The starting material II is fed into the reaction chamber in the form of its vapor, advantageously as a mixture which contains steam and may or may not contain an inert gas. Suitable gases which are inert under the reaction conditions are noble gases, eg. xenon, argon, neon and helium, alkanes, eg. methane, ethane, propane, 2,2-dimethylpropane, butane, pentane and isobutane; ethers, eg. dimethyl ether and methyl ethyl ether, and preferably, nitrogen, carbon monoxide and/or carbon dioxide and mixtures of the above. The inert gas may be introduced alone or as a mixture with steam and/or the vapor of starting material II, or, advantageously, as a mixture with air. The molar ratio of inert gas to oxygen is in particular at least 4.4:1, advantageously from 4.4:1 to 20:1 and more particularly from 6:1 to 10:1. The data relating to inert gas in each case concern the total amount, ie. including the inert gas constituent of the air used as the preferred oxidizing agent.

The oxidizing agent used can be either pure oxygen or gases containing free oxygen, especially air. The oxygen, as a rule in the form of air, and the starting material II are advantageously used in a ratio of from 0.25 to 2.5, especially from 0.5 to 1.5, moles of oxygen per mole of starting material II. Preferably, the total amount of steam used is not more than 7, advantageously from 1 to 5, moles per mole of starting material II. The air, with or without inert gas, can be introduced directly into the system used to vaporize the starting material II, advantageously into a boiling mixture of starting material II and water, or can be introduced at any other point upstream of the catalyst. The residence time in the reaction chamber is advantageously from 0.005 to 0.5, more particularly from 0.01 to 0.2, and preferably from 0.01 to 0.1, second.

The total thickness of the catalyst bed is advantageously from 10 to 50, preferably from 15 to 40, millimeters. The catalyst particles, in the form of silver crystals, are advantageously present in the reactor (which is usually vertical) in one bed or, more advantageously, in an upper and lower layer (according to particle size) of the total bed or preferably in an upper, middle and lower layer (according to particle size) of the total bed. The total catalyst bed advantageously rests on a gauze of silver or of previously annealed stainless steel. In large reactors, having a diameter of more than 15 cm, the gauze is advantageously corrugated before being fitted. Advantageously, the gauze rests on a perforated plate, immediately below which there is, advantageously, a water cooler. The starting mixture of vapor of II, inert gas and oxygen or air, with or without steam, is in general passed downward through the reactor so that the upper layer or upper layers denote the part (of the catalyst bed) which faces the starting mixture. In reactors of different construction, or where the starting mixture follows a different path, all statements in the description relating to the upper (lower) part of the catalyst apply correspondingly to the parts facing the starting mixture (the discharged mixture), for example to the front (rear) part of the catalyst in the case of horizontal reactors. If the catalyst comprises only one layer, the latter contains silver crystals of particle size from 0.1 to 2.5 millimeters, advantageously from 0.1 to 2 millimeters, preferably from 0.2 to 1 millimeter. In a 2-layer catalyst the upper layer advantageously contains from 40 to 80, preferably from 50 to 75, percent by weight of the catalyst, the particle sizes being from 0.1 to 0.75 millimeter, whilst the lower layer contains from 20 to 60, preferably from 25 to 50, percent by weight of the catalyst, the particle sizes being from 0.75 to 2.5 millimeters, advantageously from 0.75 to 1 millimeter.

In a 3-layer catalyst, the lower layer advantageously contains from 20 to 40, preferably from 25 to 35, percent by weight of all catalyst particles, the middle layer contains from 40 to 70, preferably from 40 to 60, percent by weight of all catalyst particles and the upper layer contains from 10 to 30, preferably from 15 to 25, percent by weight of all catalyst particles. The particles in the lower layer have sizes of from 0.75 to 2.5, preferably from 0.75 to 1, millimeters, those of the middle layer have sizes of from 0.4 to 0.75 millimeter and those of the upper layer have sizes of from 0.1 to 0.4 millimeter.

Advantageously, the throughput used is from 0.1 to 3 tonnes, especially from 0.2 to 1.5 tonnes, of vapor of II per m$^2$ of catalyst bed cross-section per hour. For large-scale industrial operation, the catalyst bed diameter is preferably at least 0.05 meter, advantageously from 0.1 to 3 meters. The reaction is advantageously carried out continuously at from 450° to 700° C., preferably from 475° to 650° C., especially from 500° to 625° C., under atmospheric or superatmospheric pressure. The reaction can be carried out in the absence of additional solvents, but organic solvents which are inert under the reaction conditions can also be used. Examples of suitable solvents are aromatic hydrocarbons, eg. toluene, benzene, ethylbenzene, o-, m- and p-xylene, isopropylbenzene, and methylnaphthalene; ethers, for example ethyl propyl ether, methyl tert.-butyl ether, n-butyl ethyl ether, di-n-butyl ether, diisobutyl ether, diisoamyl ether, diisopropyl ether, cyclohexyl methyl ether, diethyl ether, ethylene glycol dimethyl ether, tetrahydrofuran and dioxane; ketones, eg. methyl ethyl ketone, acetone, diisopropyl ketone, diethyl ketone, methyl isobutyl ketone, mesityl oxide, acetophenone, cyclohexanone, ethyl isoamyl ketone, diisobutyl ketone, methylcyclohexanone and dimethylcyclohexanone; aliphatic and cycloaliphatic hydrocarbons, eg. heptane, pinane, nonane, gasoline fractions having a boiling range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; and mixtures of the above. The solvent is advantageously used in an amount of from 50 to 1,000 percent by weight, preferably from 100 to 300 percent by weight, based on starting material II.

The oxidation may be carried out as follows: the starting material II, with or without water and/or organic solvent, is introduced, separately or as a mixture, into a vaporization apparatus, for example a falling film vaporizer, and are vaporized therein, advantageously at from 70° to 280° C. The gaseous mixture of vapor of II and air, with or without inert gas and steam, in the above amounts, is passed through the catalyst at the reaction temperature. The process is in general carried out continuously at pressures of from 0.5 to 3 bar, preferably from 0.8 to 1.8 bar. Advantageously, the silver catalyst is heated to 250°–500° C., preferably to 380°–450° C., before starting the process. The start of the exothermic reaction is advantageously ascertained by adding air to the starting mixture and examining the temperature change in the catalyst. If the reaction starts, a rise in temperature is immediately observed; if it does not start, the introduction of the cold air lowers the temperature. The temperature is advantageously measured in the catalyst, by means of thermocouples. Once the reaction has started, the air is in general introduced continuously into the vapor starting mixture, if appropriate by passing it through the material in the bottom of the vaporization apparatus. It is advantageous to cool the reaction gases leaving the catalyst zone rapidly, for example to 20°–160° C. This condenses the greater part of the end product. The cooled gas mixture is then advantageously fed to an absorption tower in which the end product is washed out of the gas mixture, advantageously in counter-current, by means of a suitable solvent, eg. dimethylformamide, dimethylsulfoxide, acetone, methanol or water or a mixture of these and/or by means of condensate from previous reactions. The end product I is then isolated from the condensate and the absorbates in the conventional manner, for example by distillation.

The aromatic and araliphatic aldehydes obtainable by the process of the invention are valuable starting materials for the preparation of dyes, pesticides, plastics and scents. Regarding their use, reference may be made to the above publications.

In the Examples which follow, parts are by weight.

EXAMPLE 1

An installation comprising a vaporizer and a vertical tubular reactor is used. At its top, the reactor comprises the inlet for the vapor starting mixture, and the reactor cover. The catalyst bed is located below the reactor top, and a cooling zone is provided below the catalyst bed. The reactor is connected to 4 absorption columns.

A catalyst comprising 84 parts of silver crystals of the following composition is introduced into the reactor:

|  | Proportion of the catalyst (% by weight) | Particle size mm |
|---|---|---|
| Layer 1 | 20 | 0.1–0.4 |
| Layer 2 | 50 | 0.4–0.75 |
| Layer 3 | 30 | 0.75–1 |

The height of the catalyst bed is 30 mm. Per hour, a mixture of 250 parts of benzyl alcohol, 100 parts of water and 210 parts of air is fed to the vaporizer and the benzyl alcohol and water are vaporized. The vapor starting material is passed through the catalyst and reacted at 600° C. and 1.1 bar. The residence time is 0.055 second and the throughput is 0.36 tonne/m².h. The reaction mixture is then cooled to 30° C. The combined organic phases of the condensate and of the water-operated absorption columns give 208 parts per hour of benzaldehyde (in the form of an 86 percent strength by weight solution), corresponding to a yield of 85% of theory, based on starting material II employed. The conversion is 98 percent and the space-time yield is 10 g of benzaldehyde per cm³ of catalyst volume per hour.

EXAMPLE 2

The same installation as in Example 1 is used. A catalyst comprising 84 parts of silver crystals of the following composition is introduced into the reactor.

|  | Proportion of the catalyst (% by weight) | Particle size mm |
| --- | --- | --- |
| Layer 1 | 65 | 0.1–0.75 |
| Layer 2 | 35 | 0.75–1 |

The height of the catalyst bed is 30 mm. Using a similar method to Example 1, a mixture of 560 parts of p-tert.-butylbenzyl alcohol and 120 parts of water with 270 parts of air and 380 parts of nitrogen as the inert gas is passed, per hour, over the catalyst at 520° C. and 1.1 bar. The residence time is 0.025 second and the throughput 0.8 tonne/m².h.

Using a similar method to Example 1, 398 parts of p-tert.-butylbenzaldehyde (in the form of a 90 percent strength by weight organic phase) are obtained per hour, corresponding to a yield of 72% of theory. The conversion is 98 percent and the space-time yield is 18 grams of p-tert.-butylbenzaldehyde per cm³ of catalyst volume per hour.

EXAMPLE 3

The same installation as in Example 1 is used. Using a similar method to Example 1, a mixture of 900 parts of p-methylbenzyl alcohol and 900 parts of acetone is evaporated per hour and passed, together with 890 parts of air and 200 parts of nitrogen as the inert gas, over the catalyst at 620° C. and 1.2 bar. The residence time is 0.015 second and the throughput 1.3 tonnes/m².h. The reaction is carried out similarly to Example 1. 666 parts of p-tolylaldehyde (in the form of a 43 percent strength by weight solution) are obtained per hour, corresponding to a yield of 75% of theory. The conversion is 99 percent and the space-time yield is 31 grams per cm³ of catalyst volume per hour.

EXAMPLE 4

The same installation as in Example 1 is used. Using a similar method to Example 1, a mixture of 320 parts of m-dimethylaminobenzyl alcohol and 50 parts of water with 300 parts of air is passed per hour over the catalyst at 530° C. and 1.2 bar. The residence time is 0.035 second and the throughput 0.45 tonne/m².h. 228 parts of m-dimethylaminobenzaldehyde (in the form of an 88 percent strength by weight organic phase) are obtained per hour, corresponding to a yield of 72% of theory. The conversion is 94 percent and the space-time yield is 11 grams of m-dimethylaminobenzaldehyde per cm³ of catalyst volume per hour.

EXAMPLE 5

The same installation as in Example 1 is used. A catalyst comprising 82 parts of silver crystals of particle sizes from 0.1 to 2.5 mm is introduced, as a homogeneous bed, into the reactor. The height of the catalyst bed is 30 mm. Using a similar method to Example 1, a mixture of 150 parts of 2-phenylethanol and 60 parts of water with 210 parts of air is passed per hour over the catalyst at 540° C. and 1.1 bar. The residence time is 0.07 second and the throughput 0.2 tonne/m².h. 99 parts of phenylacetaldehyde (in the form of a 73 percent strength by weight organic phase) are obtained per hour, corresponding to a yield of 67% of theory. The conversion is 78 percent and the space-time yield is 5 grams of phenylacetaldehyde per cm³ of catalyst volume per hour.

EXAMPLE 6

Using a similar method to Example 1, a mixture of 150 parts of 2-phenyl-1-propanol with 60 parts of nitrogen and 185 parts of air is passed per hour over the catalyst at 550° C. and 1.1 bar. The residence time is 0.08 second and the throughput is 0.2 tonne/m².h. 108 parts of 2-phenylpropanal (in the form of a 78 percent strength by weight organic phase) are obtained per hour, corresponding to a yield of 73% of theory. The conversion is 92 percent and the space-time yield is 5 grams of 2-phenylpropanal per cm³ of catalyst volume per hour.

EXAMPLE 7

Using a similar method to Example 1, a mixture of 300 parts of 3-(p-tert.-butylphenyl)-2-methyl-1-propanol and 200 parts of water with 250 parts of air and 250 parts of nitrogen is passed per hour over the catalyst at 560° C. and 1.1 bar. The residence time is 0.025 second and the throughput is 0.42 tonne/m².h. 211 parts of 3-(p-tert.-butylphenyl)-2-methylpropanal (in the form of a 77 percent strength by weight organic phase) are obtained per hour, corresponding to a yield of 71% of theory. The conversion is 95 percent and the space-time yield is 10 grams of 3-(p-tert.-butylphenyl)-2-methylpropanal per cm³ of catalyst volume per hour.

EXAMPLE 8

Using a similar method to Example 1, a mixture of 400 parts of 3,4,5-trimethoxybenzyl alcohol and 400 parts of acetone with 380 parts of air is passed per hour over the catalyst at 530° C. and 1.2 bar. The residence time is 0.04 second and the throughput is 0.57 tonne/m².h. 302 parts of 3,4,5-trimethoxybenzaldehyde (in the form of a 44 percent strength by weight solution) are obtained per hour, corresponding to a yield of 76% of theory. The conversion is 95 percent and the space-time yield is 14 grams of 3,4,5-trimethoxybenzaldehyde per cm³ of catalyst volume per hour.

EXAMPLE 9

Using a similar method to Example 1, a mixture of 200 parts of 4-(hydroxymethyl)-benzyl alcohol and 400 parts of dioxane with 290 parts of air is passed per hour over the catalyst at 600° C. and 1.1 bar. The residence time is 0.05 second and the throughput is 0.3 tonne/m².h. 124 parts of terephthaldialdehyde (in the form of a 22 percent strength by weight solution) are obtained per hour, corresponding to a yield of 63% of theory. The conversion is 92 percent and the space-time yield is 6 grams of terephthaldialdehyde per cm$^3$ of catalyst volume per hour.

We claim:

1. A process for the continuous preparation of aromatic and araliphatic aldehydes by oxidizing araliphatic alcohols in the presence of a metal catalyst at an elevated temperature, wherein an araliphatic alcohol is oxidized with oxygen at from 450° to 700° C. in the presence of silver crystals of particle size from 0.1 to 2.5 millimeters.

2. The process of claim 1, wherein the oxidation is carried out with a ratio of from 0.25 to 2.5 moles of oxygen per mole of starting material II.

3. The process of claim 1, wherein the oxidation is carried out with a total amount of steam of not more than 7 moles per mole of starting material II.

4. The process of claim 1, wherein the oxidation is carried out with a residence time in the reaction chamber of from 0.005 to 0.5 second.

5. The process of claim 1, wherein the oxidation is carried out with a residence time in the reaction chamber of from 0.01 to 0.2 second.

6. The process of claim 1, wherein the oxidation is carried out with a total catalyst bed thickness of from 10 to 50 millimeters.

7. The process of claim 1, wherein the oxidation is carried out with a bed of silver crystals of particle size from 0.1 to 2 millimeters.

8. The process of claim 1, wherein the oxidation is carried out with a 2-layer catalyst of which the upper layer comprises from 40 to 80 percent by weight of the catalyst and contains particles of size from 0.1 to 0.75 millimeter and the lower layer comprises from 20 to 60 percent by weight of the catalyst and contains particles of size from 0.75 to 2 millimeters.

9. The process of claim 1, wherein the oxidation is carried out with a 3-layer catalyst and the lower layer contains from 20 to 40 percent by weight of all catalyst particles, the middle layer from 40 to 70 percent by weight of all catalyst particles and the upper layer from 10 to 30 percent by weight of all catalyst particles, the particles in the lower layer having sizes of from 0.75 to 2.5 millimeters, those of the middle layer from 0.4 to 0.75 millimeter and those of the upper layer from 0.1 to 0.4 millimeter.

10. The process of claim 1, wherein the oxidation is carried out with from 0.1 to 3 tonnes of vapor of II per m$^2$ of catalyst bed cross-section per hour.

11. The process of claim 1, wherein the oxidation is carried out at from 475° to 650° C.

12. The process of claim 1, wherein the oxidation is carried out with from 50 to 1,000 percent by weight, based on starting material II, of organic solvents which are inert under the reaction conditions.

* * * * *